(12) United States Patent
Nitkowski et al.

(10) Patent No.: US 8,992,836 B2
(45) Date of Patent: Mar. 31, 2015

(54) CAVITY-ENHANCED ON-CHIP ABSORPTION SPECTROSCOPY

(75) Inventors: Arthur Nitkowski, Ithaca, NY (US); Michal Lipson, Ithaca, NY (US)

(73) Assignee: Cornell University, Ithaca, NY (US)

( * ) Notice: Subject to any disclaimer, the term of this patent is extended or adjusted under 35 U.S.C. 154(b) by 205 days.

(21) Appl. No.: 12/619,326

(22) Filed: Nov. 16, 2009

(65) Prior Publication Data

US 2010/0124787 A1 May 20, 2010

Related U.S. Application Data

(60) Provisional application No. 61/114,761, filed on Nov. 14, 2008.

(51) Int. Cl.
*G01N 21/00* (2006.01)
*G01N 21/77* (2006.01)

(52) U.S. Cl.
CPC .... *G01N 21/7746* (2013.01); *G01N 2021/7786* (2013.01)
USPC ............. 422/82.11; 385/12; 385/38; 436/164

(58) Field of Classification Search
None
See application file for complete search history.

(56) References Cited

U.S. PATENT DOCUMENTS

| | | | |
|---|---|---|---|
| 5,220,403 A | 6/1993 | Batchelder et al. | |
| 5,577,137 A | 11/1996 | Groger et al. | |
| 6,757,463 B2 | 6/2004 | Hutchinson et al. | |
| 7,079,240 B2 | 7/2006 | Scherer et al. | |
| 7,095,010 B2 | 8/2006 | Scherer et al. | |
| 7,177,492 B2 | 2/2007 | Strecker | |
| 7,212,701 B2 | 5/2007 | Strecker | |
| 7,248,771 B2 | 7/2007 | Schmidt et al. | |
| 7,266,271 B2 | 9/2007 | Strecker et al. | |
| 7,271,379 B2 | 9/2007 | Fan et al. | |

(Continued)

FOREIGN PATENT DOCUMENTS

| EP | 1535047 | 6/2005 |
|---|---|---|
| EP | 1535047 A1 | 6/2005 |

(Continued)

OTHER PUBLICATIONS

Li, C. et al. Experimental demonstration of waveguide-coupled round-cornered octagonal microresonators in silicon nitride, 2005, Opt. Lett., vol. 30(5), pp. 546-548.*
Rafizadeh, D. et al. Waveguide-coupled AlGa/GaAs microcavity ring and disk resonators with high finesse and 21.6-nm free spectral range, 1997, Optics Letters, vol. 22(16), pp. 1244-1246.*

(Continued)

*Primary Examiner* — Robert Xu
(74) *Attorney, Agent, or Firm* — Perkins Coie LLP

(57) ABSTRACT

Embodiments of optofluidic devices or methods according to the application can provide on-chip, label-free, massively parallel analysis of analytes. An embodiment of the optofluidic device can comprise a microresonator, a waveguide optically coupled to the microresonator, and a fluidic channel that exposes an analyte to an evanescent field from the microresonator, wherein the light signal has a linewidth lesser than the width of at least one resonance of the light signal propagating in the microresonator. The light signal can be tuned across a spectrum of light wavelengths, wherein the spectrum of wavelengths includes one or more wavelengths defining the at least one resonance in the microresonator. The light transmission through the waveguide over the spectrum of wavelengths of the input light can be detected, and an absorption spectrum of the analyte can be determined.

29 Claims, 3 Drawing Sheets

(56) References Cited

U.S. PATENT DOCUMENTS

| | | |
|---|---|---|
| 7,535,573 B2 | 5/2009 | Kachanov et al. |
| 7,538,881 B2 | 5/2009 | Ye et al. |
| 2004/0091212 A1 | 5/2004 | Strecker et al. |
| 2004/0146431 A1 | 7/2004 | Scherer et al. |
| 2005/0201659 A1 | 9/2005 | Strecker |
| 2006/0239606 A1 | 10/2006 | Strecker |
| 2007/0140638 A1 | 6/2007 | Yang et al. |
| 2007/0237460 A1 | 10/2007 | Fan et al. |
| 2008/0074660 A1 | 3/2008 | Ye et al. |
| 2009/0263912 A1 | 10/2009 | Yang et al. |
| 2009/0269002 A1 | 10/2009 | Wong et al. |

FOREIGN PATENT DOCUMENTS

| | | |
|---|---|---|
| EP | 1942341 A1 | 7/2008 |
| WO | WO-2008033763 A2 | 3/2008 |
| WO | WO-2008110927 A2 | 9/2008 |
| WO | WO-2009070849 A1 | 6/2009 |
| WO | WO-2009084721 A1 | 7/2009 |

OTHER PUBLICATIONS

Van, V. et al. Propagation loss in single-mode GaAs-AlGaAs microring resonators: measurement and model, 2001, Journal of Lightwave Technology, vol. 19(11), pp. 1734-1739.*

"Cavity-enhanced on-chip absorption spectroscopy using microring resonators" Arthur Nitkowski, Long Chen, Michal Lipson Aug. 4, 2008, vol. 16, No. 16, Optics Express.

Armani, A.M., et al., "Heavy water detection using ultra-high-Q microcavities," Optics Letters, 31(12):1896-1898, Jun. 2006.

Boyd, R.W., et al., "Sensitive disk resonator photonic biosensor," Applied Optics, 40(31):5742-5747, Nov. 2001.

Farca, G., et al., "Cavity-enhanced laser absorption spectroscopy using microresonator whispering-gallery modes," Optics Express, 15(25):17443-17448, Dec. 2007.

Hu, J., et al., "Fabrication and testing of planar chalcogenide waveguide integrated microfluidic sensor," Optics Express, 15(5):2307-2314, Mar. 2007.

* cited by examiner

1

CAVITY-ENHANCED ON-CHIP ABSORPTION SPECTROSCOPY

CROSS REFERENCE TO RELATED APPLICATIONS

This application claims benefit under U.S.C. 119(e) of U.S. Provisional Application No. 61/114,761, filed Nov. 14, 2008, entitled "Cavity-Enhanced On-Chip Absorption Spectroscopy", which is incorporated herein by reference in its entirety.

FIELD OF THE INVENTION

The invention relates to absorption spectroscopy in general and specifically to miniature absorption spectroscopy systems for on-chip use in chemical analysis and biological analyte detection.

BACKGROUND OF THE INVENTION

Detection, identification, and analysis of analytes using absorption spectroscopy are known at a macroscopic scale. Such processes require light to interact with an examined analyte for a period of time easily achieved at macroscopic levels. Generally, a setup comprises a fixed length, single pass optical path through an analyte, in which some sort of light source inputs light through the optical path, and some sort of detector detects the light at the end of the optical path.

Miniaturizing optofluidic devices to the microscopic scale potentially enables greater portability, lower analyte consumption for testing, and greater potential for massively parallel measurements. Parallel measurements are identical or substantially identical measurement methods performed with multiple replications of the same apparatus. These measurements can be performed simultaneously, in parallel, and with small devices, they can be designed to perform them in massive quantities. Therefore, incorporating advanced fluid handling techniques at the micron scale with highly sensitive photonic devices has the potential to provide compact, effective sensors for lab-on-a-chip tools, which can also be used to perform massively parallel measurements.

At least partly for these reasons, optofluidic techniques in which microfluidics are integrated with photonic components are gaining more use in biosensing and chemical analysis applications. Many optofluidic transduction methods for sensing and analysis have been demonstrated, including refraction, absorbance, fluorescence, surface-plasmon-resonance, and interferometric measurements. Absorbance-based optofluidic techniques are particularly attractive because they can offer a potential to provide label-free spectral information for detection and identification of the analyte.

On the negative side, miniaturizing microfluidic devices comprised in absorption spectroscopy devices reduces the optical path length and light absorption, and therefore, the sensitivity of the system. In order to mitigate this problem or attempt to achieve the sensitivity of macroscopic systems, some devices have used slow-light photonic crystals or specific waveguide geometries.

One method to address the shortened interaction of light in optofluidic devices on the microscopic scale consists of the use of a microresonator, which is a geometrically shaped waveguide, such as a ring, that allows light to resonate and cycle through the waveguide, before being coupled out of the device to some sort of detector. Resonating the light around the microresonator extends the optical path length of the light interacting with the analyte, and therefore the sensitivity of the device.

Current spectroscopy devices using microresonators have not reached great efficiency or realized the full advantage of their small scale. Some devices defeat the advantage of being small by using some large scale components or requiring other components that could be eliminated. In at least one example of such a device, the device requires detection of light interacting with an analyte at a particular wavelength, and requires multiple, differently sized resonators to obtain spectral information of the analyte at various wavelengths. This device would be many times the size of a device that did not require multiple resonators to obtain spectral information of an analyte for a range of wavelengths (e.g. an absorption spectrum). The ability to conduct massively parallel measurements is also decreased due to the increased size in obtaining, for example, an absorption spectrum. In another example, a device uses a light source that emits a broadband light whose spectral width extends across many resonant wavelengths of light in the microresonator. This device requires the use of a spectrometer to separate different wavelengths in order to ultimately provide an absorption spectrum for the analyte.

It would be advantageous to use one or more cavity-enhanced microresonators in a microfluidic device for absorption spectroscopy by reducing components and size or avoiding large scale components that decrease portability, increase size, and/or decrease the ability to conduct massively parallel measurements.

SUMMARY OF THE INVENTION

There is provided embodiments of an optofluidic device that can provide completely on-chip, label-free, massively parallel analysis of analytes. In one embodiment, the device enables measurement of the absorption spectrum of less than 2 nL of an analyte with resolutions possible at less than 1 nm and sensitivity equivalent to that of macroscopic systems.

In another embodiment of the invention, an optofluidic device is provided that comprises a microresonator, a waveguide optically coupled to the microresonator, and a light signal having a linewidth lesser than the width of at least one resonance of the light in the microresonator. The light source is tunable across a spectrum of light wavelengths, wherein the spectrum of wavelengths includes at least one wavelength defining the at least one resonance.

In another embodiment, an optofluidic apparatus is provided that comprises a microfluidic channel, a plurality of microresonators, a plurality of waveguides, and at least one light signal having a linewidth lesser than the linewidth of at least one from the plurality of microresonators. The at least one light signal can tune continuously at a rate across a spectrum of wavelengths at which the at least one light signal resonates within at least one from the plurality of microresonators. Each waveguide from the plurality of waveguides is optically coupled with one microresonator from the plurality of microresonators, and each microresonator from the plurality of microresonators is positioned, at least partly, in the microfluidic channel.

In yet another embodiment, a method is provided for measuring an absorption spectrum of an analyte. The method comprises providing a microresonator, providing a waveguide optically coupled to the microresonator, providing a source of light optically coupled to the waveguide, tuning the source of light, detecting light transmitted through the waveguide, and determining an absorption spectrum. The light source emits the light with a linewidth narrower than the width of at least one resonance in the microresonator. The light source is tuned across a spectrum of light wavelengths that produces the at least one resonance of the light in the microresonator.

DETAILED DESCRIPTION OF THE INVENTION

There is described an optofluidic absorption spectroscopy apparatus in which a range of input optical waveforms (i.e. input light) are subjected to an analyte and the absorption spectrum is measured and calculated. The input light couples with a microresonator. The light resonates through the microresonator, thereby increasing the optical path length, increasing the duration the light is exposed to the analyte, and increasing the resulting degree of sensitivity in measuring the absorption spectrum.

Figure 1:
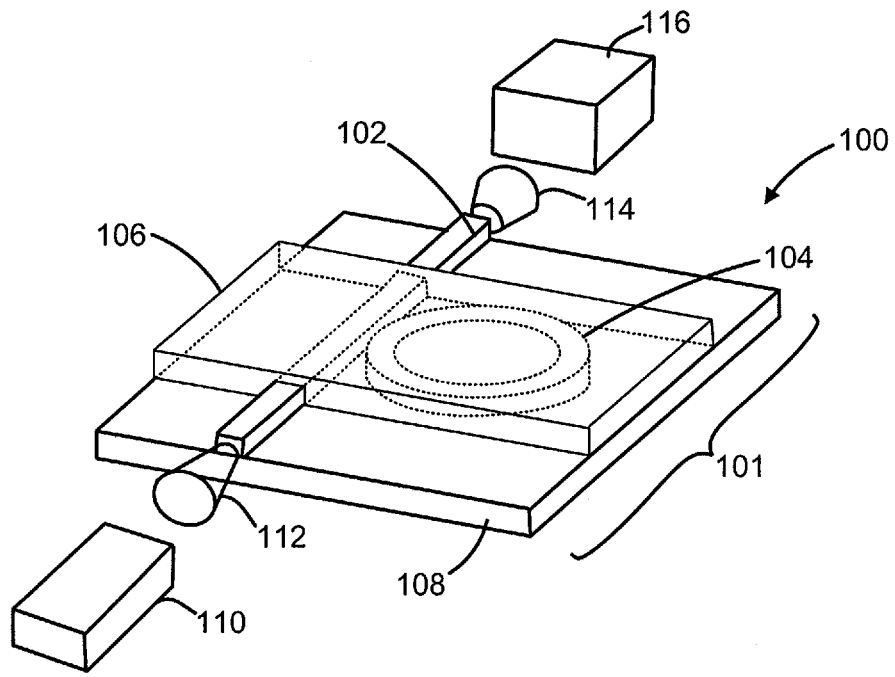
FIG. 1 is a schematic diagram of an absorption spectroscopy apparatus according to one embodiment of the invention.

An example of an on-chip optofluidic absorption spectroscopy apparatus 100 according to the present description is shown in FIG. 1. The optofluidic absorption spectroscopy apparatus 100 can comprise an optofluidic portion 101, which can comprise a coupling waveguide 102, a resonator 104, a fluidic channel 106, and a base 108. Further, the absorption spectroscopy apparatus 100 can also comprise a light source 110, an input coupling lens 112, an output coupling lens 114, and a photo-detector 116.

The light source 110 can be, for instance, a tunable, narrow linewidth laser. A narrow linewidth laser emits a light with a narrow range of wavelengths or frequencies as compared to the range of wavelengths or frequencies defining the width of each resonance in the microresonator 104. The width of a resonance in the microresonator 104 can be expressed as its linewidth, which can be expressed in terms of the range of wavelengths or frequencies over the width of a resonance. In one exemplary embodiment, in which the microresonator 104 has a quality factor (Q factor) of 100,000 at a wavelength of 1550 nm, and the linewidth of the microresonator 104 is approximately 2 gigahertz (GHz), the linewidth of the light source 110 can be sufficiently narrower than 2 GHz, so that multiple points can be recorded within the range of wavelengths (or range of frequencies) that define the width of each resonance. For example, a laser light source 110 with a linewidth of 150 kilohertz (kHz), which is several orders of magnitude smaller than 2 GHz, enables the resolution of over 10,000 measurement wavelengths or frequencies in the 2 GHz range.

The light source 110 optically couples with the coupling waveguide 102 so that light emitted from the light source 110 enters the coupling waveguide 102. The input coupling lens 112 can increase the coupling efficiency when coupling light from the light source 110 to the coupling waveguide 102. The input coupling lens 112 can be, for instance, a tapered lens fiber.

The coupling waveguide 102 is capable of transmitting light. In the exemplary embodiment depicted in FIG. 1, the coupling waveguide 102 is a planar waveguide, constructed from silicon. However, the coupling waveguide 102 can be another sort, such as an optical fiber, and can be constructed from alternate materials that transmit light. The coupling waveguide 102 can be oxide clad to provide a symmetric index profile to increase input light coupling and reduce waveguide losses. The coupling waveguide 102, which in the exemplary embodiment is spaced 300 nm from the resonator 104, couples at least a portion of the light received from the light source 110 into the resonator 104.

This distance between the coupling waveguide 102 and the resonator 104 can be increased or decreased depending, at least in part, on the desired optical behavior in the device 100 (e.g. the amount of coupling), as well as the optical characteristics of the waveguide 102 and the resonator 104. Generally, as the distance between the coupling waveguide 102 and the resonator 104 is increased, the amount of light coupling between the waveguide 102 and the resonator 104 is decreased. When losses due to coupling to the coupling waveguide 102 equal the round trip resonator losses, critical coupling can occur. If higher coupling, lower coupling, or critical coupling, for instance, are desired, then the spacing between the waveguide 102 and the resonator 104 can be adjusted accordingly.

The resonator 104 can be constructed of optically transparent material shaped so as to constrain light to a repeating path and simultaneously support a multitude of optical resonances. Possible materials out of which the resonator 104 can be constructed include, for example, silica, glass, quartz, gallium, silicon, silicon nitride, or combinations and derivations thereof. The exemplary resonator 104 depicted in FIG. 1, along with the coupling waveguide 102, can be made of silicon. This material is an example of material adequately suited for operating the device with light wavelengths in the infrared (IR) spectrum. Absorption spectroscopy in the visible spectrum might be accomplished by constructing photonic components out of silicon nitride ($Si_3N_4$), for instance, or another suitable material with a high refractive index (e.g. approximately 2.0), and low absorption in the visible spectrum (e.g. between about 400 nm to about 700 nm).

While the resonator 104 of the exemplary embodiment depicted in FIG. 1 is a microring resonator, it is conceived that any suitable microresonator geometry can be used. Exemplary geometries include but are not limited to a photonic-crystal cavity, a disc, a torus, a cylinder, or a spheroid. In the exemplary embodiment depicted in FIG. 1, the resonator 104 is a microring with a radius of 100 μm, and with a Q factor greater than 100,000. A resonator with a higher Q factor has lower damping.

The resonator 104 illustrated in FIG. 1 has a cross section dimensioned at 450 nanometers (nm) wide by 250 nm high. The coupling waveguide 102 is dimensioned similarly at 450 nm by 250 nm. Other dimensions are possible. These dimensions in the exemplary embodiment support a single mode at 1.5 micrometers.

Referring still to FIG. 1, the radius of the resonator 104 is dimensioned at approximately 100 micrometers. This radius can vary to achieve desired quantities of certain qualities, such as size and resolution. The radius and circumference affect the FSR between resonance wavelengths. The FSR between resonance wavelengths, at least in part, determines the resolution of measurements with the device 100. Therefore, the circumference and radius can be altered to affect the resolution. Increasing the circumference and radius achieve a higher resolution and a larger footprint, while decreasing the circumference and radius decreases the resolution and makes the device more compact.

Referring still to FIG. 1, the resonator 104 is positioned on a base 108 (e.g. a substrate, a wafer, or a chip) so that the resonator 104 is positioned in the path of the fluidic channel 106. The fluidic channel 106 can be a microfluidic channel on the scale of the resonator 104. An analyte solution containing chemical or biological material flows in or occupies at least a portion of the fluidic channel 106, so that the resonator 104 is positioned in the analyte solution. In the present example, the analyte solution covers the resonator 104 so that the resonator 104 can be fully submerged and cladded in the analyte solution. However, in other embodiments, the analyte solution might only cover a portion of the resonator 104, such as the side(s), or the bottom of the resonator 104.

Figure 2:
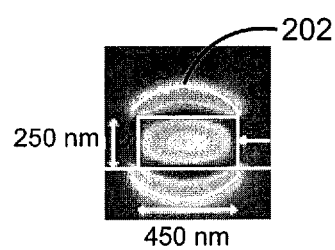
FIG. 2 is a sectional view of a waveguide (e.g. resonator) depicting an Ey mode profile for quasi transverse magnetic polarized light propagating through the waveguide.

Light from the light source 110 that is coupled into the resonator 104 propagates around the perimeter of the resonator 104 by continuous internal reflection. As the light travels around the perimeter of the resonator 104, an evanescent field of light extends slightly beyond the resonator 104. The evanescent field of light 202, according to the exemplary embodiment of FIG. 1, can be seen extending from the resonator 104 in FIG. 2. The evanescent field of light 202 that extends beyond the resonator 104 interacts with the analyte solution which surrounds the resonator 104. The light within the evanescent field interacts or reacts with the molecules of the sample as the light propagates around the perimeter of the resonator 104. In the resulting interaction or reaction between the evanescent field of light 202 and the analyte solution, absorption of the evanescent light 202 by the analyte can occur. At resonant frequencies, the light circulates many times within the resonator 104. This additional circulation time at the resonant frequencies equivocates to an enhanced length and time of interaction between the evanescent field of light 202 and the analyte.

In the exemplary embodiment, the spectroscopy apparatus was designed to increase or maximize interaction with the analyte solution in the fluidic channel 106. For instance, while the waveguide is oxide clad to contain propagating light, the resonator 104 can be unclad to increase or allow maximum interaction of the evanescent light trapped in the resonator 104 with liquid in the surrounding fluidic channel 106.

In one alternate embodiment, the analyte can bind with the surface of the resonator 104. In one such embodiment, the surface of the resonator 104 can be functionalized with a particular antibody. Pathogens can specifically bind to the functionalized surface of the resonator 104, increasing the sensitivity of the identification, detection, and analysis of these pathogens by absorption spectroscopy with the absorption spectroscopy device 100, or focusing the absorption spectroscopy measurement on these pathogens. In another such embodiment, labels such as, but not limited to, fluorescent labels or metal nanoparticles can be attached to the analyte. A measure of the quantity of light something will absorb (i.e. the extinction coefficient), is orders of magnitude higher for fluorescent labels and metal nanoparticles than some unlabeled biological or chemical analytes (e.g. some proteins). Attaching the fluorescent labels or the metal nanoparticles can increase absorption of the light, which can increase the sensitivity of the absorption spectroscopy device 100.

Light propagating through the coupling waveguide 102 exits to the photo-detector 116. In the exemplary embodiment, the exiting light is focused through the output coupling lens 114 (e.g. a microscope objective lens) onto the photo-detector 116. The photo-detector 116 then outputs signals (e.g. a voltages) to a computer processor. Signals (e.g. voltages) from the light source are also relayed to a computer processor. In the exemplary embodiment, a data acquisition (DAQ) board, manufactured by National Instruments, is used in conjunction with a computer running a program (e.g. a LabView script) to record and synchronize the signals.

In another embodiment, the light source 110 and/or photo-detector 116 can be integrated with the optical components in order to reduce or eliminate optical coupling. Optical coupling between the light source 110 and coupling waveguide 102, and between the coupling waveguide 102 and photo-detector 116 contributes to coupling noise, which adversely affects (i.e. reduces) the signal to noise ratio. The coupling noise is due, in part, to reflection at the coupling interfaces, which leads to Fabry-Perot noise. Therefore, to reduce or eliminate this coupling noise, the light source 110 and/or photo-detector 116 can be integrated with the optofluidic device to avoid or reduce optical coupling between the light source 110 and coupling waveguide 102, and between the coupling waveguide 102 and photo-detector 116. In one embodiment, the light source 110, such as but not limited to a diode laser, can be positioned on the base 108 without an input coupling lens 112, so the light can be emitted directly from the light source 110 to the coupling waveguide 102. In one embodiment, the light source 110 can be integrated into the coupling waveguide 102. Similarly, the photo-detector 116 can be positioned on the base 108 without an output coupling lens 114 so light propagates directly from the waveguide 102 to the photo-detector 116. In one embodiment, the photo-detector 116 can be integrated into the coupling waveguide 102. Using a light source and/or photo-detector that can be positioned on the base 108 with or without coupling lenses 112 and 114 also makes the device more compact and more portable.

Figure 3:
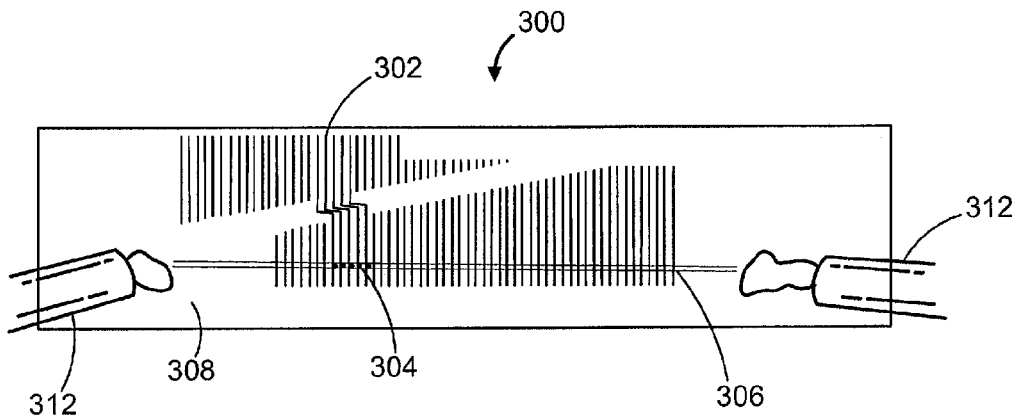
FIG. 3 is an example of a fabricated structure according to one embodiment of the invention comprising a plurality of oxide clad waveguides, a fluidic channel, a plurality of silicon microring resonators, and two inlet tubes.

The embodiment as described herein above with respect to FIG. 1 can be implemented in parallel, entailing that many measurements can be taken simultaneously. FIG. 3 illustrates one embodiment in which parallel measurements can be taken. Referring to FIG. 3, an optofluidic device 300 for absorption spectroscopy can comprise a plurality of waveguides 302, a plurality of resonators 304, at least one fluidic channel 306, and a base 308. Over 50 coupling waveguides 302 are shown, with a resonator 304 optically coupled to each. Any number of waveguides 302 and resonators 304 can be used, depending for instance on size constraints, measurement requirements, and manufacturing constraints. In the present example, the output of each coupling waveguide 302 is offset laterally from the input of each respective coupling waveguide 302 in order to reduce or prevent input light from scattering into the photo-detector 116. Each resonator 304 is situated in a straight path that is defined by a fluidic channel 306. While the fluidic channel 306 is straight in this embodiment, it can be alternatively shaped, for instance, to build a device 300 that complies with physical space or dimensional constraints of a larger system. The resonators 304, in any configuration of the fluidic channel 306, will be situated or immersed in the fluidic channel 306.

One or more fluid delivery devices 312 deliver analyte solution to the fluidic channel 306. In the present example, each fluid delivery device 312 comprises a pressure-controlling syringe pump used in conjunction with plastic tubing (e.g. Tygon tubing). Other devices can be used to drive the analyte solution. The tubing 312 delivers analyte solution to each end of the fluidic channel 306. The tubing can be pharmaceutical grade plastic, medical grade plastic, glass, or another appropriate material.

The device as seen in FIG. 1 or FIG. 3 can be fabricated using standard microfabrication techniques. While a method of fabricating the presently described absorption spectroscopy apparatus is described below, the method and apparatus are not intended to be limited thereby.

The present example uses a silicon-on-insulator wafer with a 3 μm buried oxide layer for the base and a 250 nm device layer to fabricate the optical structures (e.g. the waveguides 102, and the resonators 106). Alternate fabrication materials can be used for various purposes. For instance, the use of silicon nitride can be used to extend the wavelength range of the device. Electron beam lithography and inductively coupled plasma etching can be used to create the optical structures (e.g. the waveguides 102 and resonators 106) on the wafer. Lift-off resist and then photoresist can be spun onto the wafer and patterned using contact lithography to mask the resonator 104. A 1.7 micrometer cladding layer of silicon dioxide can be evaporated over the wafer using an electron gun source and cryopumped evaporator. After dicing and polishing, the oxide and resist over the resonator 104 can be removed using a microposit photoresist remover (e.g. Microposit Remover 1165), leaving the resonator 104 exposed.

The fluidic channels 106 can be made from silicone-based organic polymer polydimethylsiloxane (PDMS) using soft lithography processes, and then aligned and bonded to the wafer. In the present example, a master mold for the fluidic channels 106 can be made by spin-coating SU-8 photoresist to a thickness of 30 micrometers on a silicon wafer. Using contact lithography, channels with a width of 300 micrometers can be patterned onto the SU-8 including alignment marks to later align the channels to the photonic devices. PDMS can be poured over the mold and baked at 80 degrees Celsius for several hours. The PDMS can be cut and peeled off the master wafer, and holes can be punched through the PDMS to act as inlet and outlet ports for fluids. The wafer and fluidics layer can be oxygen plasma cleaned before a contact aligner can be used to irreversibly bond the PDMS to the device wafer.

In the case where the resonators 304 and coupling waveguides 302 are made of silicon nitride, a bottom cladding of thermal oxide can first be grown on top of an undoped silicon wafer using wet thermal oxidation. A 200 nm layer of stoichiometric silicon nitride can then be deposited using low pressure chemical vapor deposition (LPCVD). The waveguides 302 and resonators 304 can be patterned using an electron beam lithography system followed by inductively coupled plasma reactive ion etching (ICP RIE).

The procedure for determining the spectral information of the analyte, using the above-described apparatus, or an alternate embodiment thereof, comprises tuning the wavelength of the input light source across a spectral range, or wavelength range, while simultaneously recording the transmission of the coupling waveguide, with analyte solution present in the microfluidic channel(s) 106, 306, and then using a theoretical model to determine the absorption contribution from the analyte solution cladding the resonator(s) 104, 304.

Measurements are taken first by introducing light across a range of wavelengths into the coupling waveguide(s) 102, 302. In one example, wherein the light is provided by a tunable laser, the light source 110 is tuned continuously at 1 nm per second (nm/s) from 1460 nm to 1610 nm. Alternatively, the light source 110 can be tuned in discrete increments. Other wavelength ranges are possible. For instance, the wavelength range could extend from about 1.2 micrometers to about 6 micrometers. The photo-detector 116 signals are recorded 500 times per second, providing a spectrum resolution of 2 picometers. The time to acquire the readings across the 150 nm wavelength range is 2.5 minutes. The wavelength range, the frequency of recordings, and hence, the acquisition time can all be smaller or greater. For instance, if it is desirable to more quickly acquire readings on the same wavelength range while maintaining the resolution of 2 picometers, then a faster detector can be used in conjunction with a light source 110 that tunes more rapidly through the wavelength range. If signals from the photo-detector 116 are sampled at a frequency of 50,000 times per second, and the light source 110 is tuned continuously at 100 nm/s from 1460 nm to 1610 nm, then the acquisition time would be reduced to 1.5 seconds.

During measurement of the transmission, some light will be lost in transmission due to intrinsic absorption loss in the coupling waveguide(s) 102, 302 and resonator(s) 204, 304. Transmission will also be decreased by absorption loss of the light interacting with the analyte. Light resonating in the resonator(s) 104, 304 that couples back into the coupling waveguide(s) 102, 302 interferes destructively with the light propagating through the coupling waveguide(s) 102, 302, also decreasing the light transmitted through the coupling waveguide(s) 102, 302 at resonating wavelengths of the light.

These resonances are therefore identifiable in the recorded transmissions as local valleys, indicating local minimums in light transmitted through the waveguide(s) 102, 302. These local minimums can be seen in FIG. 4, which records a transmission over a 15 nm spectral range using no analyte. A single local minimum from FIG. 4, with a peak resonance wavelength 502 can be seen in FIG. 5. To find the analyte' absorption loss contribution to the total absorption loss, the resonances are analyzed to extract the absorption loss due to the analyte.

In one example, the waveguide transmission is given by:

$$T(\theta) = \frac{a^2 + |t|^2 - 2a|t|\cos\theta}{1 + a^2|t|^2 - 2a|t|\cos\theta} \quad \text{Equation 1}$$

where a is the field attenuation coefficient, t is the field transmission coefficient at the region of coupling between the waveguide(s) 102, 302 and resonator(s) 104, 304, and θ is the phase shift per circulation of light in the resonator(s) 104, 304. The phase shift can be expressed in terms of the free space wavelength as $\theta = 2\pi L n_{eff}/\lambda$, where L is the microring resonator circumference and $n_{eff}$ is the effective index of the mode. It is beneficial to restate Equation 1 in terms of experimentally measurable quantities so that the only fitting parameters are the attenuation and transmission coefficients. Restating Equation 1 in this manner can be done by expanding the cosine term in Equation 1 for small wavelength deviations around a resonant wavelength $\lambda_0$:

$$\cos(\theta) = \cos\left(\frac{2\pi L n_{eff}}{\lambda}\right) \cong 1 - \frac{2\pi^2 L^2 n_g^2}{\lambda_0^4}(\lambda - \lambda_0)^2 \quad \text{Equation 2}$$

where L is the microring resonator circumference and the group index $n_g$ can be calculated directly from the resonance spacing using the relation $FSR = \lambda^2/n_g L$.

Fitting the theoretical curve described by Equation 1 to a resonance yields values for the attenuation and the transmission coefficients. However, because these two coefficients are interchangeable in Equation 1, it is helpful to distinguish the two coefficients. Distinguishing the attenuation coefficient and the transmission coefficient can be done by comparing the coefficient values for two microring resonators 104 of equal radius but with differently sized gaps between the microring resonator 104 and the coupling waveguide 102. The field transmission coefficients which describe light coupling will shift to lower values (greater coupling) for smaller gap distances while the attenuation coefficients will remain the same. The total absorption coefficient $\alpha_T$ for light propagating within the resonator can then be determined from the relation $a=\exp(-\alpha_T L/2)$. The total absorption is related to the absorption of the analyte solution by:

$$\alpha_T = \alpha_I + \Gamma \alpha_a \qquad \text{Equation 3}$$

Where $\alpha_I$ is the intrinsic waveguide loss, $\alpha_A$ is the absorption from the analyte, and $\Gamma$ is the confinement factor, which is a measure of how much of the total guided light is interacting with the cladding material. The confinement factor can be determined from experiment or a simulation of a waveguide's mode profile using:

$$\Gamma = \frac{n_A \int_A |E|^2 \, dA}{Z_0 \int \mathrm{Re}\{E \times H^*\} \cdot \hat{z} \, dA} \qquad \text{Equation 4}$$

where the top integral is over the analyte cladded region, $n_A$ is the refractive index of the analyte solution and $Z_0$ is the free space impedance.

Figure 4:
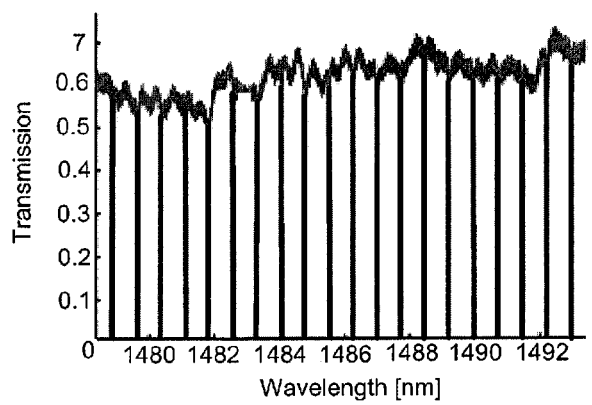
FIG. 4 depicts a 15 nm window recording of light transmission through one embodiment of the device of FIG. 1.
Figure 5:
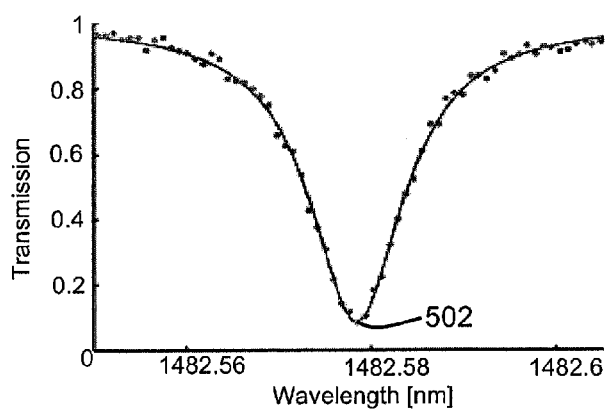
FIG. 5 depicts a curve fitting of one resonance wavelength from FIG. 4.

The intrinsic waveguide loss $\alpha_I$, if it is not already known, can be determined by tuning the wavelength of the input light source across a wavelength range while simultaneously recording the transmission of the coupling waveguide, with no analyte solution present in the fluidic channel. The measurement can be performed with the fluidic channel 106, 306 dry because the change in coupling due to the addition of fluid does not significantly alter the intrinsic waveguide loss. Each resonance is analyzed to determine the waveguide loss over the wavelength range of the input light source, with no analyte in the fluidic channel 106, 306. FIG. 5 shows an example of the curve fitting, with a loaded Q value of approximately 120,000. FIG. 4 shows a transmission window about 16 nm wide (from approximately 1478 nm to approximately 1494 nm). FIG. 5 depicts one resonance dip from the 16 nm window of FIG. 4. The points represent the detected values while the solid line represents the fitted curve.

Using methods described above, in this example, the resonance is known to be slightly undercoupled and the resulting fitting parameters are t=0.981 and a=0.967 for the field transmission and attenuation coefficients respectively. The attenuation value for the illustrated resonance corresponds to an intrinsic waveguide absorption of $\alpha_I=1.07$ centimeters$^{-1}=$ 4.67 decibels per centimeter for waveguide propagation.

Figure 6:
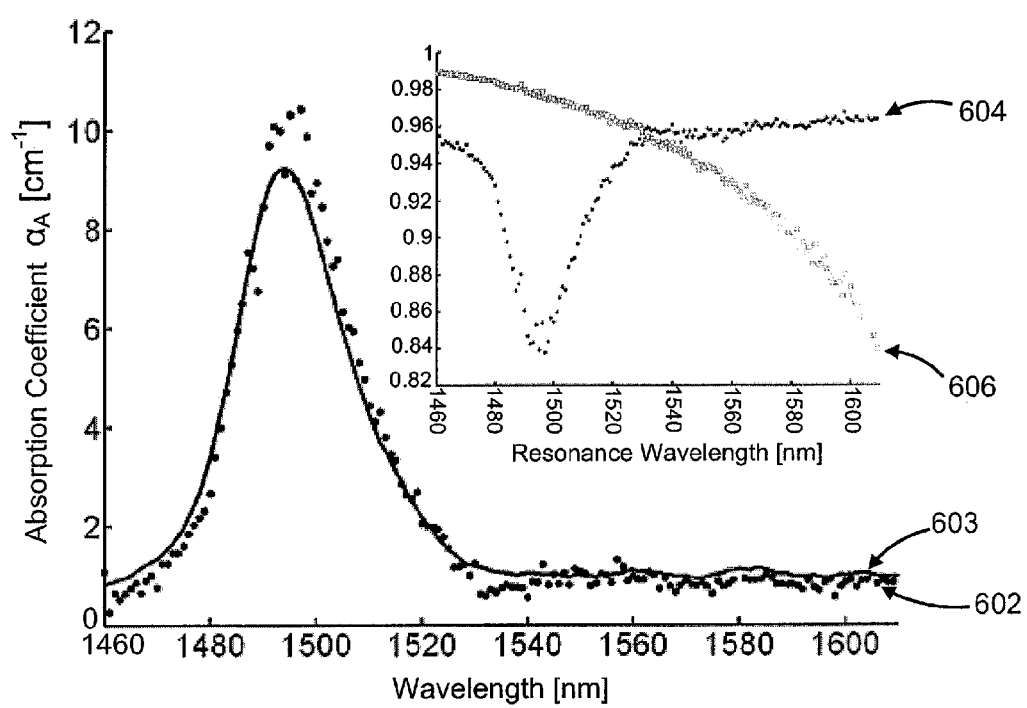
FIG. 6 depicts an absorption spectrum for an analyte according to one embodiment of the device of FIG. 1.

FIG. 6 depicts an absorption spectrum 602 of N-methylaniline. Dotted curve 602 represents the absorption spectrum as measured and calculated using the exemplary embodiment of the apparatus and the exemplary method described above. For comparison, solid curve 603 represents the absorption spectrum as measured with an existing commercial spectrometer. After determining the intrinsic waveguide loss and recording light transmitted through the apparatus across a spectral range from 1460 nm to 1610 nm, the FSR is known to be approximately 1 nm. Each resonance is curve-fitted to determine the attenuation and transmission coefficients, shown in the inset of FIG. 6, where curve 604 displays the attenuation coefficient, and curve 606 displays the transmission coefficient. Once the total absorption is known, the absorption contribution from the analyte can be determined using equation 3 and subtracting the intrinsic absorption. The confinement factor for the waveguide in the exemplary embodiment is calculated from Equation 4 using a refractive index of 1.56 for N-methylaniline.

While the present invention has been described with reference to a number of specific embodiments, it will be understood that the true spirit and scope of the invention should be determined only with respect to claims that can be supported by the present specification. Further, while in numerous cases herein wherein systems, apparatuses, and methods are described as having a certain number of elements, it will be understood that such systems, apparatuses and methods can be practiced with fewer than the mentioned certain number of elements.

We claim:

1. An optofluidic device for measuring an absorption spectrum of an analyte, comprising:
   a microfluidic channel for containing said analyte;
   a microresonator positioned at least partially in said microfluidic channel and at least partially immersible in said analyte;
   a waveguide optically coupled to said microresonator, said waveguide having an input end and an output end,
   wherein said input end receives a first light signal having a linewidth lesser than the width of at least one resonance of said first light signal propagating in said microresonator,
   wherein said first light signal is continuously tunable at a rate across a spectrum of wavelengths including one or more wavelengths that define said at least one resonance of said first light signal in said microresonator;
   a light source that generates said first light signal tunable across said spectrum of wavelengths, wherein said light source outputs said first light signal to said waveguide; and
   a photo-detector that receives a second light signal exiting said output end of said waveguide, wherein said second light signal at different wavelengths of said spectrum of wavelengths measures the transmission spectrum of said first light signal through said waveguide, said microresonator and said analyte;
   a mechanism that (1) uses said measured transmission spectrum to determine a total attenuation coefficient and a transmission coefficient by applying a curve fitting to said measured transmission spectrum, wherein said total attenuation coefficient measures the total light absorption caused by said waveguide, said microresonator and said analyte; and (2) obtains a net absorption spectrum resulting from absorption by said analyte by subtracting an intrinsic absorption coefficient from said total absorption coefficient across said spectrum of wavelengths, wherein said intrinsic absorption coefficient measures light absorption caused by said waveguide and said microresonator without presence of said analyte across said spectrum of wavelengths; and
   a second microresonator positioned at a second coupling distance to said waveguide that is different from a first coupling distance between said microresonator and said waveguide, wherein said microresonator and said second microresonator are used to distinguish said total attenuation coefficient and said transmission coefficient.

2. The optofluidic device of claim 1, further comprising a substrate, wherein said microfluidic channel, said microresonator, said waveguide, and at least one of said light source and said photo-detector are positioned on said substrate.

3. The optofluidic device of claim 1, wherein at least one of said light source and said photo-detector is integrated into said waveguide to reduce noise caused by optical coupling.

4. The optofluidic device of claim 1, further comprising:
a) an input coupling lens optically coupling said first light signal emitted from said light source to said input end of said waveguide; and
b) an output coupling lens focusing said second light signal exiting said output end of said waveguide onto said photo-detector.

5. The optofluidic device of claim 1, wherein said spectrum of wavelengths is in the infrared spectrum.

6. The optofluidic device of claim 1, wherein said spectrum of wavelengths is in the visible light spectrum.

7. The optofluidic apparatus of claim 1, wherein a surface of said resonator is functionalized with an antibody.

8. The optofluidic apparatus of claim 1, wherein said microresonator and said waveguide comprise silicon nitride ($Si_3N_4$).

9. An optofluidic apparatus for measuring an absorption spectrum of an analyte, comprising:
a microfluidic channel for containing said analyte;
a plurality of microresonators, each microresonator being positioned at least partially in said microfluidic channel and at least partially submersible in said analyte; and
a plurality of waveguides, each waveguide being optically coupled to one microresonator of said plurality of microresonators, each waveguide having an input end and an output end, wherein said input end receives a first light signal having a linewidth lesser than the linewidth of at least one of said plurality of microresonators, wherein said first light signal tunes continuously at a rate across a spectrum of wavelengths at which said first light signal resonates within said at least one from the plurality of microresonators, and wherein each waveguide includes an input waveguide section connected to the input end, an output waveguide section connected to the output end and an offset waveguide section connecting the input waveguide section and the output waveguide section to cause an offset between the output waveguide section and the input waveguide section, thus reducing scattering of light in the input waveguide section into the output waveguide section.

10. The optofluidic apparatus of claim 9, further comprising:
at least one light source tunable across said spectrum of wavelengths, wherein said at least one light source outputs said first light signal to said plurality of waveguides; and
at least one photo-detector that receives a second light signal exiting said output end of said plurality of waveguides, wherein said at least one photo-detector outputs at least one signal value usable to calculate an absorption loss in said at least one microresonator; and
a mechanism that uses output of each photo-detector at different wavelengths within said spectrum of wavelengths, that is produced while said light source is being tuned for generating said first light signal tunable across said spectrum of wavelengths, to obtain measurements of total light absorption caused by said waveguide, said microresonator and optical absorption by said analyte across said spectrum of wavelengths, and to apply a curve fitting based on light absorption caused by said waveguide and said microresonator without presence of said analyte across said spectrum of wavelengths to obtain said net absorption amplitude of said second light signal resulting from absorption by said analyte by adjusting for light lost in transmission due to intrinsic absorption loss in said waveguide and said microresonator.

11. The optofluidic device of claim 1, wherein said waveguide and said microresonator are spaced from each other by a gap that is between about 0nm and about 300 nm.

12. The optofluidic device of claim 11, wherein said waveguide and said microresonator are spaced from each other by a gap that is about 300 nm.

13. The optofluidic device of claim 1 wherein said microresonator and said wave guide are identical in cross-sectional height and width.

14. The optofluidic device of claim 13 wherein each of said microresonator and said wave guide is about 250 nm in height and about 450 nm in width.

15. The optofluidic apparatus of claim 9 wherein each microresonator includes an exterior surface that is functionalized to bind with a selective material in said analyte.

16. The optofluidic apparatus of claim 9 wherein each microresonator is optically coupled to the output waveguide section of a respective waveguide.

17. The optofluidic apparatus of claim 9 wherein said microresonator includes an exterior surface that is functionalized to bind with a selective material in said analyte.

18. The optofluidic apparatus of claim 9, further comprising:
at least one light source emitting a broadband light having wavelengths across said spectrum of wavelengths, wherein said at least one light source outputs said first light signal to said plurality of waveguides;
at least one photo-detector that receives a second light signal downstream from said output section of said plurality of waveguides; and
a mechanism that uses output of each photo-detector at different wavelengths within said spectrum of wavelengths to obtain measurements of total light absorption caused by said waveguide, said microresonator and optical absorption by said analyte across said spectrum of wavelengths, and to apply a curve fitting based on light absorption caused by said waveguide and said microresonator without presence of said analyte across said spectrum of wavelengths to obtain said net absorption amplitude of said second light signal resulting from absorption by said analyte by adjusting for light lost in transmission due to intrinsic absorption loss in said waveguide and said microresonator.

19. The optofluidic apparatus of claim 18, further comprising:
a spectrometer positioned to receive the broadband light from a waveguide to separate the received broadband light into different light signals at different wavelengths.

20. An optofluidic apparatus for measuring an absorption spectrum of an analyte, comprising:
a light source that generates light having wavelengths across a spectrum of wavelengths;
a microfluidic channel configured to carry an analyte;
a microresonator positioned at least partially in the microfluidic channel and at least partially immersible in the analyte, the microresonator configured to have one or more optical resonances within the spectrum of wavelengths of the light source;
a waveguide optically coupled to the microresonator and configured to include an input waveguide section that receives the light from the light source, an output waveguide section to output light coming from the input waveguide and an offset waveguide section connecting the input waveguide section and the output waveguide section to cause an offset between the output waveguide section and the input waveguide section, thus reducing scattering of light in the input waveguide section into the output waveguide section; and a photo-detector that receives output light exiting the output waveguide section of the waveguide and converts the received output light into a detector output; and a mechanism that uses output of the photo-detector at different wavelengths within the spectrum of wavelengths of the light source to obtain measurements of total light absorption caused by the waveguide, the microresonator and optical absorption by the analyte across the spectrum of wavelengths, to apply a curve fitting to measured light absorption caused by the waveguide and the microresonator without presence of the analyte which is obtained by performing a dry measurement on said waveguide and said microresonator across the spectrum of wavelengths, and to determine a net optical absorption by the analyte by adjusting for light lost in transmission due to intrinsic absorption loss in the waveguide and the microresonator.

21. The optofluidic apparatus as in claim 20, wherein the microresonator includes an exterior surface that is functionalized to bind with a selective material in the analyte.

22. The optofluidic apparatus as in claim 20, wherein the light source emits a broadband light across the spectrum of wavelengths.

23. The optofluidic apparatus as in claim 22, further comprising:
a spectrometer positioned between the output section of the waveguide and the photo-detector to receive the broadband light from the output section of the waveguide and configured to separate the received broadband light into different light signals at different wavelengths.

24. The optofluidic apparatus as in claim 20, wherein the light source is tunable to tune the wavelength of the emitted light across the spectrum of wavelengths.

25. An optofluidic device for measuring an absorption spectrum of an analyte, comprising:
a broadband light source that generates broadband light of different wavelengths across a spectrum of wavelengths;
a microfluidic channel configured to carry an analyte;
a microresonator positioned at least partially in the microfluidic channel and at least partially immersible in the analyte, the microresonator configured to have optical resonances within a spectrum of the broadband light of different wavelengths;
a waveguide optically coupled to the microresonator and configured to include an input waveguide section that receives the light from the light source and an output waveguide section to output light coming from the input waveguide;

a photo-detector that receives output light downstream from the output waveguide section of the waveguide and converts the received output light into a detector output, wherein said detector output across said spectrum of wavelengths measures the transmission spectrum of said broadband light through said waveguide, said microresonator and said analyte; and a mechanism that (1) uses said measured transmission spectrum to determine a total attenuation coefficient and a transmission coefficient by applying a curve fitting to said measured transmission spectrum, wherein said total attenuation coefficient measures the total light absorption caused by said waveguide, said microresonator and said analyte; and (2) obtains a net absorption spectrum resulting from absorption by said analyte by subtracting an intrinsic absorption coefficient from said total absorption coefficient across said spectrum of wavelengths, wherein said intrinsic absorption coefficient measures light absorption caused by said waveguide and said microresonator without presence of said analyte across said spectrum of wavelengths; and a second microresonator positioned at a second coupling distance to said waveguide that is different from a first coupling distance between said microresonator and said waveguide, wherein said microresonator and said second microresonator are used to distinguish said total attenuation coefficient and said transmission coefficient.

26. The optofluidic apparatus as in claim 20, further comprising:
a spectrometer positioned between the waveguide and the photo-detector to receive the broadband light from the output section of the waveguide and configured to separate the received broadband light into different light signals at different wavelengths.

27. The optofluidic device of claim 20, further comprising:
a substrate on which the microfluidic channel, the microresonator, the waveguide, the broadband light source and the photo-detector are positioned.

28. The optofluidic device of claim 20 wherein the broadband light source or the photo-detector is integrated with the waveguide to reduce noise caused by optical coupling.

29. The optofluidic apparatus of claim 20 wherein the microresonator includes an exterior surface that is functionalized to bind with a selective material in the analyte carried by the microfluidic channel.

* * * * *